US006110469A

United States Patent [19]

Singh et al.

[11] Patent Number: 6,110,469

[45] Date of Patent: Aug. 29, 2000

[54] HYBRID PLASMID FOR 38 KDA ANTIGEN OF *M. TUBERCULOSIS*

[75] Inventors: Mahavir Singh; Kenneth Nigel Timmis, both of Braunschweig, Germany

[73] Assignee: Gesellschaft fuer Biotechnologische Forschung mbH (GBF), Braunschweig, Germany

[21] Appl. No.: 08/102,505

[22] Filed: Aug. 5, 1993

Related U.S. Application Data

[62] Division of application No. 07/882,574, May 13, 1992, abandoned.

[30] Foreign Application Priority Data

May 17, 1991 [DE] Germany ............................ 41 16 249

[51] Int. Cl.[7] ......................... A61K 39/04; A61K 39/00; C07K 1/00; C07K 16/00

[52] U.S. Cl. .................... 424/248.1; 424/92; 424/184.1; 424/192.1; 424/203.1; 530/350; 530/412; 530/413; 530/417; 530/418; 530/422; 435/69.3

[58] Field of Search .................................. 424/92, 248.1, 424/192.1, 203.1; 435/69.3; 530/350, 412, 413, 417, 418, 422

[56] References Cited

PUBLICATIONS

Lazar et al. Mol. Cell biology 8(3):1247–1252, Mar. 1988.
Burgess et al. J. Cell Biology 111:2129–38, Nov. 1990.
Singh et al. Gene 117(1):53–60 Aug. 1992.
McCarthy et al. Molecular Microbiology 2:455–65 1988.
Verbon et al. Scand. J. Immunol. 36:371–84 (Mar. 1992).
Schauder et al. Gene 52(1):279–83 1987.
Andersen et al. Infection and Immunity 57(8):2481–88 1989.
Young et al. Infection and Immunity 54(1): 177–83 1986.
Deres et al. Nature 342:561–564 1989.
Wiker et al. Journal of General Microbiology 137(4): 875–84 Apr. 1991.
Sambrook, J. Molecular Cloning, A Laboratory Manual, 2nd Edition pp. 17.37–17.41 1989.

*Primary Examiner*—Nita Minnifield
*Attorney, Agent, or Firm*—Kane, Dalsimer, Sullivan, Kurucz, Levy, Eisele and Richard, LLP

[57] ABSTRACT

The invention concerns a hybrid plasmid for the expression of unfused 38 kDa antigen of *M. tuberculosis* in *E. coli, E. coli* with the plasmid, an 38 kDa antigen and a protein of about 33 kDa useful for diagnoses.

12 Claims, 9 Drawing Sheets

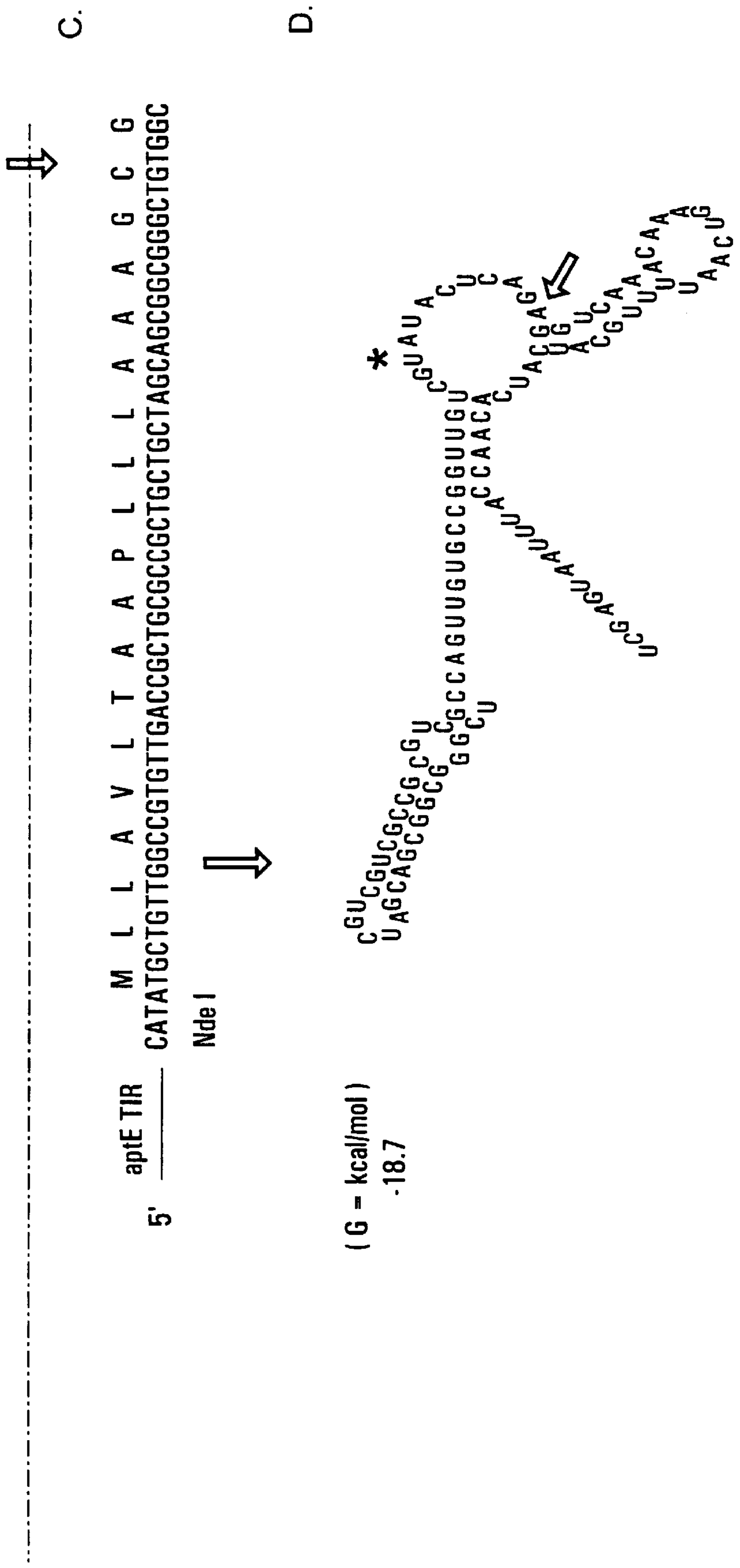
F I G. 1(b)

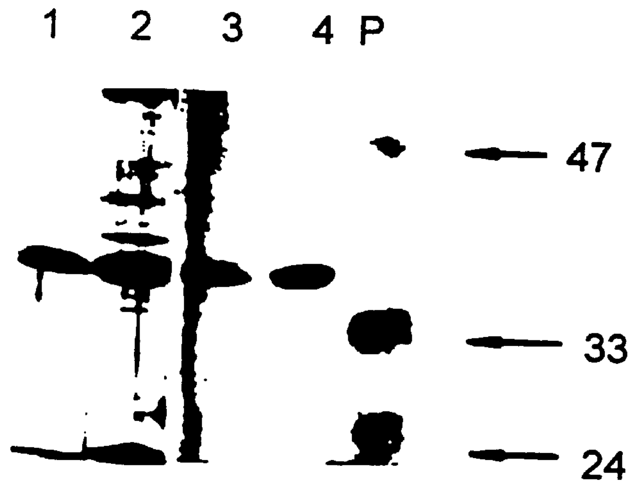
F I G. 7A
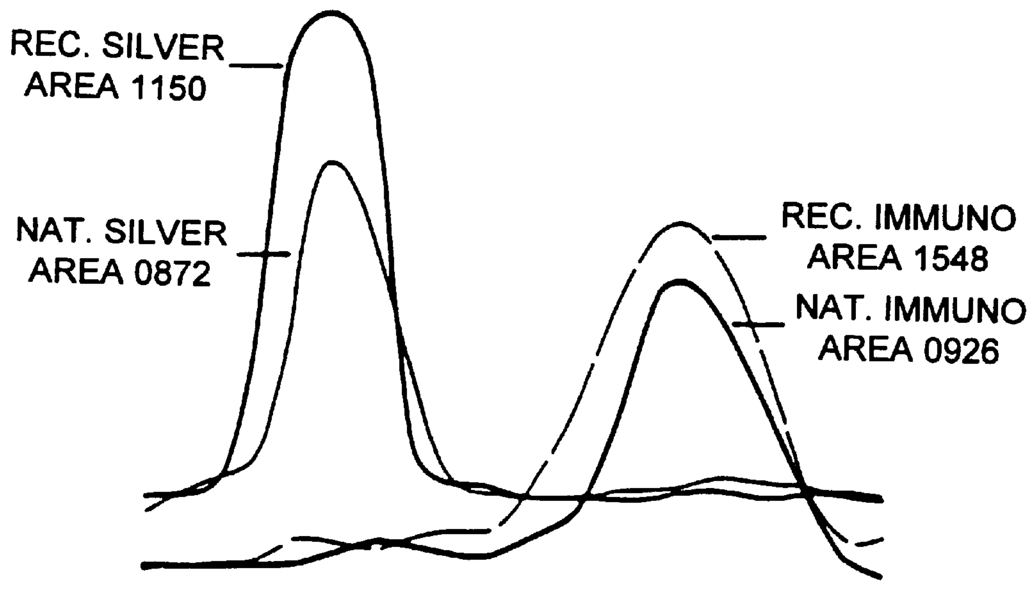
F I G. 7B

```
                              SEQUENCE LISTING


(1) GENERAL INFORMATION:

   (iii) NUMBER OF SEQUENCES:  1


(2) INFORMATION FOR SEQ ID NO: 1:

     (i) SEQUENCE CHARACTERISTICS:
          (A) LENGTH:          78 base pairs
          (B) TYPE:            nucleic acid
          (C) STRANDEDNESS:    single
          (D) TOPOLOGY:        linear

    (ii) MOLECULE TYPE:        antigen

   (iii) HYPOTHETICAL:

    (iv) ANTI-SENSE:           no

     (v) FRAGMENT TYPE:

    (vi) ORIGINAL SOURCE:
          (A) ORGANISM:         M. Tuberculosis
          (B) STRAIN:
          (C) INDIVIDUAL ISOLATE:
          (D) DEVELOPMENTAL STAGE:
          (E) HAPLOTYPE:
          (F) TISSUE TYPE:
          (G) CELL TYPE:
          (H) CELL LINE:
          (I) ORGANELLE:

   (vii) IMMEDIATE SOURCE:
          (B) CLONE:

    (xi) SEQUENCE DESCRIPTION: SEQ ID NO: 1:

CATATGAAAA TTCGTTTGCA TACGCTGTTG GCCGTGTTGA CCGCTGCGCC                50

GCTGCTGCTA GCAGCGGCGG GCT                                             73
```

HYBRID PLASMID FOR 38 KDA ANTIGEN OF *M. TUBERCULOSIS*

CROSS-REFERENCE TO RELATED APPLICATION

This application is a division of U.S. patent application Ser. No. 07/882,574 filed May 13, 1992 and now abandoned.

BACKGROUND OF THE INVENTION

1. Field of the Invention

The invention relates to polypeptides and more particularly to the 38 kDa antigen of *M. tuberculosis.*

2. Brief Description of Related Art

Tuberculosis is a highly contagious human disease with over 3 million deaths and 8 million new cases occurring annually. The advent of AIDS is expected to worsen the situation because of reactivation of the dormant *M. tuberculosis* in immunocompromised individuals. The infectious dose in tuberculosis is exceedingly low, e. g. one to three tubercle bacilli are sufficient to initiate a primary lesion in the lung. The diagnosis of the infected individuals plays a vital role in the epidemiology and prevention and spread of the disease. Currently, diagnosis rests on the cultivation of *M. tuberculosis* from the sputum which takes about 6 weeks because of the slow growth rate of the organism. Another important part of the diagnosis is the 'Tuberculin-test'. Tuberculin or the purified protein derivative (PPD) is a mixture of proteins from heat killed *M. tuberculosis* culture filtrate. This test suffers from high non-specificity due to cross-reactions in individuals infected with or vaccinated with other mycobacteria. Thus, there is an obvious need for developing defined and specific sero-diagnostic and skin-testing reagents for tuberculosis.

Serological studies have shown that the 38 kDa antigen of *M. tuberculosis* contains immunodominant epitopes specific to the virulent strains of *M. tuberculosis*. This antigen is produced in minor quantities in the vaccine strain BCG which is an avirulent derivative of the bovine-tubercle bacillus *M. bovis*. Thus, on the basis of serology, this antigen can be used to distinguish between organisms of *M. tuberculosis* complex and other mycobacteria. Purification of the native 38 kDa antigen directly from *M. tuberculosis* is not practicable because of the low yields, slow growth rates and the virulent nature of the organism.

As already stated, *Mycobacterium tuberculosis* is the causative agent of tuberculosis, a widespread human disease claiming about 3 million lives each year. Important goals of mycobacterial research are the provision of protective immunity against tuberculosis through more effective vaccines, and the development of specific skin-test/serodiagnostic reagents. A pre-requisite of such goals is the characterization and detailed evaluation of the immunological role of individual mycobacterial antigens. For this purpose, substantial amounts of such antigens are required. Purification of antigens directly from *M. tuberculosis* is difficult because of low cell yields, slow growth rates and the virulent nature of the organism (Kadival, G. V., S. D. Chaparas, and D. Hussong. 1987. Characterization of serologic and cell-mediated reactivity of a 38 kDa antigen isolated from *Mycobacterium tuberculosis*. J. Immunol. 139: 2447–2451. Young, D., L. Kent, A. Rees, J. Lamb, and J. Ivanyi. 1986. Immunological activity of a 38 kDa-kilodalton protein purified from *Mycobacterium tuberculosis*. Infect. Immun. 54: 177–183). A potential solution to this problem is the production of recombinant antigens in biotechnologically emanable organisms such as *E. coli.*

The immunological and diagnostic relevance of the 38 kDa protein antigen of *M. tuberculosis* has been shown previously (Andersen, A. B., Z.-L. Yuan, K. Haslov, B, Vergmann, and J. Bennedsen. 1986. Interspecies reactivity of five monoclonal antibodies to *Mycobacterium tuberculosis* as examined by immunoblotting and enzyme-linked immunosorbent assay. J. Clin. Microbiol. 23: 446–451; Young, D. et al. 1986. supra.). The protein contains species specific B-cell epitopes (Anderson, A. B. et al., supra.), and T-cells isolated from immunized mice, guinea pigs or humans proliferate when cultivated in its presence (Kadival, G. V. et al. 1987. supra.; Worsaae, A., L. Ljungqvist, K. Haslov, I. Heron, and J. Bennedsen. 1987. Allergenic and blastogenic reactivity of three antigens from *Mycobacterium tuberculosis* in sensitized guinea pigs. Infect. Immmun. 55: 2922–2927; Young, D. et al. 1986. supra.). The majority of humans (especially of the HLA type DR2), suffering from active tuberculosis develop antibodies against the 38 kDa antigen (Bothamley, G. H., J. S. Beck, G. M. T. Schreuder, J. D'Amaro, R. R. P. de Vries, T. Kardijito, and J. Ivanyi. 1989. Association of tuberculosis and *Mycobacterium tuberculosis*—specific antibody level with HLA. J. Infect. Dis. 19: 549–555).

The 38 kDa protein of the Gram positive bacterium *Mycobacterium tuberculosis* H37Rv is an immunodominant antigen of potential utility for diagnosis and vaccine development. Assessment of this potential requires large amounts of the purified protein that would be difficult if not impossible to obtain from *M. tuberculosis* itself.

SUMMARY OF THE INVENTION

According to one embodiment of the invention, a hybrid plasmid for the expression of an unfused 38 kDa antigen of *M. tuberculosis* in *E. coli* is provided, the plasmid comprising

- the signal sequence of the 38 kDa antigen (pre-protein) and
- a restriction site comprising within its recognition sequence the base triplet ATG which codes the first amino acid M in frame.

According to one specific embodiment of the invention the hybrid plasmid is characterized in that the 38 kDa antigen is a protein of *M. tuberculosis* of a wild type or of a variant of *M. tuberculosis* which likewise causes tuberculosis.

The signal sequence comprises for example 17, 18, 19, 20, 21, 22, 23 or 24 codons.

According to a specific embodiment the hybrid plasmid is characterized in that the DNA sequence coding the 38 kDa antigen (pre-protein) is inserted N-terminally in a NcoI-, NdeI- or SphI restriction sequence of the starting vector for example pJLA 603.

Examples of DNA sequences coding the 38 kDa antigen (pre-protein) are given in FIGS. 1A and 1C.

According to another embodiment the invention is directed to *E. coli* comprising a hybrid plasmid according to the invention.

According to another embodiment the invention is directed to a 38 kDa antigen (pre-protein) of *M. tuberculosis* which can be produced by means of *E. coli* comprising a hybrid plasmid according to the invention, the signal sequence comprising 17 to 24 codons, a signal sequence of 23 codons being excluded.

The 38 kDa antigen (pre-protein) according to the invention can be characterized by 22 to 17 amino acids of the following signal sequence (SEQ ID NO.1):

MKIRLHTLLAVLTAAPLLLAAAG for example amino acid 1 plus amino acids 8 to 23.

According to another embodiment the invention is directed to a protein of about 33 kDa which can be obtained by means of *E. coli* as host of pJLA 603 as expression plasmid

- a DNA sequence coding the 38 kDa antigen of *M. tuberculosis* (pre-protein) being inserted into a NcoI, NdeI or SphI restriction site of pJLA 603,
- the inserted DNA sequence comprising the signal sequence of the antigen,
- the recognition sequence of the restriction site of the base triplett comprising ATG, coding the first codon M in frame and
- if wanted, the protein of about 33 kDa being separated from the simultaneously expressed 38 kDa antigen.

According to a specific embodiment of the invention a protein of about 33 kD is characterized in that it is deleted N-terminally by the signal sequence and additional 24 amino acids compared with the 38 kDa antigen of *M. tuberculosis* (pre-protein).

According to another embodiment the invention concerns a 38 kDa antigen of *M. tuberculosis* and/or a protein of about 33 kDa produced by means of *E. coli* comprising a hybrid plasmid according to the invention and being renaturated as follows:

- solubilization of the antigen and/or protein, obtained as inclusion body, in guanidine-HCl (if wanted in the presence of a reducing agent) and
- subsequent renaturation by means of cross-linked dextran; SEPHADEX chromatography.

According to a specific embodiment of the invention

- the solubilization is carried out with about 6 M guanidine-HCl and/or in the presence of dithiothreithol (DTT) and/or
- the renaturation is carried out by means of sephadex G-25.

According to the invention recombinant plasmids have been constructed which produce high levels of the 38 kDa antigen of *M. tuberculosis* in *Escherichia coli*. With the inventive recombinant constructions, large quantities of the unfused (unique) 38 kDa protein can be produced in *E. coli* mostly in the form of inclusion bodies. According to the invention a method for the isolation and purification of the recombinant antigen and inclusion bodies has also been developed. The purified 38 kDa antigen thereby prepared is immunologically indistinguishable from the native 38 kDa antigen of *M. tuberculosis*. Due to its high specificity to *M. tuberculosis*, this recombinant antigen may be useful for the serological diagnosis of tuberculosis worldwide. The antigen is also a potential candidate for vaccines against tuberculosis because it contains immunodominant T-cell epitopes.

The gene coding for the 38 kDa antigen had been previously cloned and in the present study was expressed as an unfused protein in *Escherichia coli* under the control of strong transcriptional (bacteriophage lambda $P_RP_L$) and translational (atpE) signals. Fermentation of the recombinant *E. coli* K-12 strain CAG629 (pMS9-2), which is deficient in on protease and the heat shock response, produced the recombinant antigen at high levels (about 10% of total cellular protein). The recombinant antigen, which accumulated as inclusion bodies, was completely solubilized in 6 M guanidine-HCl, refolded and purified to apparent homogeneity. The product showed the expected amino acid composition and molecular weight, and as strong reactivities with three different monoclonal antibodies as the native protein. Polyclonal antibodies raised against the recombinant antigen reacted strongly with the native antigen in enzyme-linked immunosorbent assay. These results demonstrated that recombinant 38 kDa antigen which cannot be distinguished antigenically from the native protein of *M. tuberculosis* can be prepared in quantity from *E. coli.*

BRIEF DESCRIPTION OF THE DRAWINGS

FIG. 7. Comparison of the native and the recombinant 38 kDa antigen. A, about 1 μg of the affinity purified native protein (lanes 1, and 3) and the recombinant protein preparation-I (lanes 2, and 4) were separated on SDS-12.5% PAGE and either silver stained (lanes 1, and 2) or immunoblotted using MAb HBT12 (lanes 3, and 4). Lane P indicates the pre-stained molecular weight standard. B, Laser densitometric comparison of the immunoreactivity of the native and the recombinant 38 kDa protein. The silver stained gel and the immunoblot shown in A were scanned with a laser densitometer. Peak areas of the silver stained native (Nat. Silver) and the recombinant protein (Rec. Silver), as well as those of the immunoblotted native (Nat. Immuno) and the recombinant protein (Rec. Immuno) are shown.

A DETAILED DESCRIPTION OF THE INVENTION FOLLOWS

MATERIAL AND METHODS

Figure 1A:
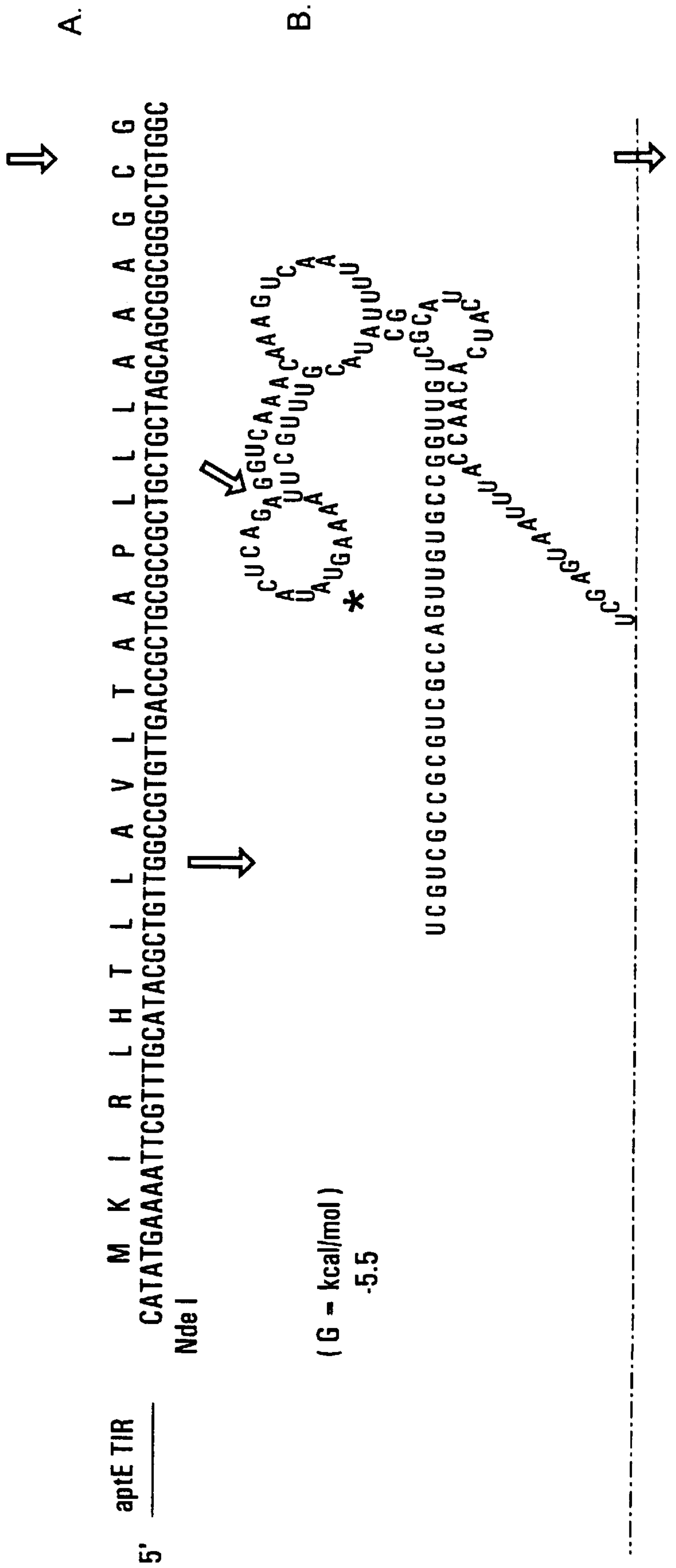
FIG. 1. Nucleotide sequences of the 5'-end of engineered genes encoding the pre-form (A) and truncated form (C) of the 38 kDa protein. The NdeI (CATATG) site was created by oligonucleotide mutagenesis using the oligonucleotide 5'-AGCACAGAAAGGTATCATATGAAAATTCGTTTG CATA-3' (for A) SEQ ID NO.1 and the oligonucleotide 5'-ATTCGTTTGCATATGCTGTTGGCC GTGT-3' (for C) SEQ ID NO.2. The predicted amino acid sequence is presented in one letter code and the arrow above the sequence shows the putative processing site. The RNA stability in the region of the ATG start codon of the pre-form (B) and the truncated form (D) was calculated by the method of Zucker and Stiegler (Zucker, M., and P. Stiegler. 1981. Optimal computer folding of large RNA sequences using thermodynamics and auxiliary information. Nucl. Acids Res. 9: 133–148). The ribosome binding site of the atpE gene and the initiation codon of the 38 kDa-antigen gene is marked with a star and a triangle, respectively.

Bacterial Strains, Phage, Plasmids and Growth Conditions

The *E. coli* strains used in this study were TG-1 (lac-pro, supE, thi, hsdD5/F'traD36, proA$^+$ B$^+$, lacI$^q$, lacZ M15) DH5alpha(endA1, recA1, hsdR17, supE44, thi-1, gyrA96, relA1, (lacZYA-argF), 80d/lacZ M15), EC 538 and CAG629 (lon, htpR165-Tn10; C. Gross). The recombinant lambda gt11 bacteriophage clone AA59 was isolated in a previous study (Andersen, A. B., A. Worsaae, and S. D. Chaparas. 1988. Isolation and characterization of recombinant lambda gt11 bacteriophages expressing eight different mycobacterial antigens of potential immunological relevance. Infect. Immun. 56: 1344–1351) from an *M. tuberculosis* genomic DNA library constructed by R. A. Young (Young, R. A., B. R. Bloom, C. M. Grosskinsky, J. Ivanyi, D. D. Thomas, and R. W. Davis. 1985. Dissection of *Mycobacterium tuberculosis* antigens using recombinant DNA. Proc. Natl. Acad. Sci. USA 82: 2583–2587).

Unless otherwise stated, the strains were grown in Luria-Bertani broth (Maniatis, T., E. F. Fritsch, and J. Sambrook. 1982. Molecular cloning: a laboratory manual. Cold Spring Harbor Laboratory, Cold Spring Harbor, N.Y.) at 37° C. Liquid cultures were aerated by shaking at 160 r.p.m. in a Pilot-Shake shaker (Kühne, Switzerland).

DNA Manipulations

Preparation and handling of DNA was according to standard protocols (Maniates, T., supra.). Transformation was performed as described by Hanahan (Hanahan, D. 1983. Studies on transformation of *Escherichia coli* with plasmids. J. Mol. Biol. 166: 557–580). DNA sequencing was done by the dideoxynucleotide chain termination method (Sanger, F., S. Nicklen, and A. R. Coulson. 1977. DNA sequencing with chain-terminating inhibitors. Proc. Natl. Acad. Sci. USA 74: 5463–5467). Oligonucleotides were synthesized using an Applied Biosystems model 380B DNA synthesizer and purified with OPC columns (Applied Biosystems Inc.).

Oligonucleotide Mutagenesis

The 2.0 kb EcoRI fragment from the genomic clone lambda AA59 (Anderson, A. B. et al., 1988, supra) was transferred into M13mp19. Preparation of single stranded DNA and oligonucleotide mutagenesis was carried out using the Amersham kit (RPN 1523). The DNA sequence of the template before and after mutagenesis was confirmed by DNA sequencing (Sanger, F., supra.).

Small-Scale Preparation of Crude Protein Extracts

Strains were grown in LB medium containing ampicillin (100 μg/ml) at 30° C. to an absorbance at 580 nm of 0.6. Cultures were induced by shifting to 42° C. for 3 h in a shaking water bath. Bacteria were harvested from 1 ml culture, suspended in 100 μl of sample buffer (62 mM Tris-HCL, pH 6.8; 2% sodium dodecyl sulphate; 0.7 M 2.mercaptoethanol; 10% glycerol; 0.002% bromophenol blue) and broken by sonication in ice (3×30 sec; 50 W) using a Braun Labsonic 2000. Samples were heated at 95° C. for 10 min and 10 μl were analysed by polyacrylamide gel electrophoresis.

Cultivation in a Bioreactor 30 l of a modified concentrated LB medium (tryptone, 40 g/l; yeast extract, 20 g/l; NaCl, 5 g/l) were sterilized in a 50 l bioreactor (Biostat U30D, Braun Melsungen, FRG) in the presence of 3.5 ml Ucolub N38(polyalkylene-glycol) anti-foam (Brenntag, Mülheim, FRG). Cultivation was initiated by inoculation with a 0.5 l overnight culture of the organism in the same medium to give an initial $A_{546}$=0.04. Stirrer speed was maintained constant at 300 rpm, which ensured a dissolved oxygen concentration close to saturation, and pH was held at 6.9. After 4 hours of fermentation ($A_{546}$=0.4) the temperature was shifted from 30° C. to 42° C., and maintained at this temperature for a further 4 hours. At the end of the induction period the broth was concentrated in a closed system by crossflow microfiltration (Enka module type A7 ABA 3A) with 0.23 $m^2$ Accural membrane (0.2 μm pore diameter; Enka, Wuppertal, FRG) until a final volume of 10 l was obtained.

Protein Purification

Cells obtained from the bioreactor were disrupted by single pass through a high pressure homogenizer LAB 60/500/2 (A. P. V. -Schröder, Lübeck, FRG) at 500 bar with a flow rate of 60 l/h. Inclusion bodies were crudely separated using a centrifugal separator SA 1-01-175 (Westfalia, Oelde, FRG). This device allows isolation of inclusion bodies from the broth at a flow rate of 15–20 l/h. The inclusion bodies were washed twice with 200 ml of buffer L (50 mM Tris-HCl, 10 mM EDTA, pH 8.0) containing 2% TRITON X-100, supra. Washed pellets were resuspended in 3 l of buffer L containing 6M guanidine-HCl, 20 mM DTT for 16 hrs at 4° C. with slow stirring. After centrifugation at 7000 g, the supernatant fluid was passed through a Sephadex G-25 gel filteration column (10×90 cm) equilibrated with 10 mM Tris-HCl buffer, pH 7.0, containing 100 mM sodium chloride in order to remove the guanidine-HCl and effect renaturing of the recombinant antigen. The solution was applied in 2 l aliquots with a flow rate of 7 l/h and the eluate was monitored for $O.D_{260}$ and conductivity. The desalted and renatured antigen solution was recovered in starting buffer with a conductivity of 8 mS $cm^{-1}$, well separated from the salt peak containing mainly guanidine-HCl. The antigen peaks were combined and diluted with distilled water to obtain a conductivity of 5 mS $cm^{-1}$ and the pH adjusted to 8.5 with 1M Tris. The solution was divided into two parts for the following purification step.

One part of the solution was applied to an FPLC-column (QAE-SEPHAROSE, supra; 5×18 cm) equilibrated with 20 mM Tris-HCl buffer, pH 8.0. The flow rate was 1.72 l/h corresponding to a linear flow rate of 86,6 cm/h. After extensive washing with the starting buffer, elution of the antigen was performed by application of a step gradient consisting of 50 mM, 100 mM, 250 mM, 500 mM and 1M sodium chloride in starting buffer. Afterwards the column was re-equilibrated with starting buffer, the second portion from the gel filtration column was applied and eluted as described before. The antigen-containing fractions from the two QAE-SEPHAROSE, supra runs were pooled, concentrated and diafiltered (2 mS $cm^{-1}$) by ultrafiltration using an Amicon Hollowfiber Cartridge (type H1P10; cutoff 10.000).

Around 20 mg of the protein obtained was applied to a Mono Q HR (5/5) FPLC-column equilibrated with 20 mM Tris-HCl, pH 8.0. The column was washed with starting buffer at a flow rate of 2 ml/min and at a pressure of 25 bar. Thereafter, the antigen was eluted by gradually increasing the sodium chloride concentration to 0.5 M in starting buffer. Altogether three Mono Q HR (5/5) runs were carried out under the conditions described above.

Polyacrylamide Gel Electrophoresis and Immunoblotting

The crude and purified proteins were analyzed by sodium lauryl sulfate/polyacrylamide (12%) gel electrophoresis (Laemmli, U. K. 1970. Cleavage of structural proteins during the assembly of the head of bacteriophage T4. Nature (London) 227: 680–683). Protein samples were mixed 1:1 with 2× sample buffer and heated at 95° C. for 10 min before loading on the gels. After electrophoresis the polypeptides were visualized by silver staining (Damerval, C., M. le Guilloux, J. Blaisonneau, and D. de Vienne. 1987. A simplification of Heukeshoven and Dernick's silver staining of proteins. Electrophoresis. 8: 158–159). Protein concentrations were determined by the method of Lowry et al. (Lowry, O. H., A. L. Farr, N. J. Rosebrough, and R. Randall. 1951. Protein measurement with the folin phenol reagent. J. Biol. Chem. 193: 265–275). Proteins were transferred to a nitrocellulose membrane (BioRad) with a home made semi-dry blotting apparatus using 25 mM Tris, 192 mM glycine, 20% methanol pH 7.4. Non-specific binding was blocked by incubating the filter in TBS (50 mM Tris-HCl; 200 mM NaCl, pH 7.5) containing a 10% solution of milk (0.3% fat). The primary antibodies (mouse monoclonal antibodies) were diluted 1000-fold in TBS and incubated with the filters. overnight at 4° C. The filters were washed 3 times with TBS and immunodetection was carried out with a biotinylated anti-mouse IgG and streptavidin-alkaline phosphatase conjugate (BRL, Gaithersburg, Md., USA). For the immunodot-blot assay, protein samples were filtered through a nitrocellulose membrane using a BioRad bio-dot apparatus and processed further as described above. Monoclonal antibodies HAT2, HBT12, HYT28 have been described earlier (Andersen, A. B., et al. 1986. supra; Ljungqvist, L., A. Worsaae, and I. Heron. 1988. Antibody responses against *Mycobacterium tuberculosis* in 11 strains of inbred mice: noval monoclonal antibody specifities generated by fusions, using spleens from BALB.B10 and CBA/J mice. Infect. Immun. 56: 1994–1998; Schou, C., Z.-L. Yuan, A. B. Andersen, and J. Bennedsen. 1985. Production and partial characterization of monoclonal hybridoma antibodies to *Mycobacterium tuberculosis*. Acta Pathol. Microbiol. Immunol. Scand. Sect. C 93: 265–272). Densitometric measurements of silver stained gels and western blots were done on a laser densitometer (LKB).

Amino Acid Analyses

Amino acid analyses were performed on a Biotronik LC-5001 amino acid analyzer (Maintal, Germany) after hydrolysis of the protein sample in 6N HCl containing 0.1 % phenol for 24 h at 105° C.

Production of Polyclonal Anti-38 kDa Protein Sera

Rabbits were immunized subcutaneously with either affinity purified 38 kDa protein (Worsaae, A., L. Ljungqvist, and I. Heron. 1988. Monoclonal antibodies produced in BALB.B10 mice define new antigenic determinants in culture filtrate preparations of *Mycobacterium tuberculosis*. Infect. Immun. 56: 2608–2614) or with recombinant 38 kDa protein (Preperation I). The antigens (10 μg per dose) were adsorbed to aluminium hydroxide (2.4 mg) and subsequently mixed with 1 ml of Freund's incomplete adjuvant. The rabbits were immunized three times with intervals of two weeks. The blood was drawn ten days after the last immunization and the IgG fraction was purified as described by Harboe and Inglid (Harboe, N., and A. Inglid. 1983. Immunization, isolation of immunoglobulins and antibody titre determination. Scand. J. Immunol. 17S10: 345–351).

Electron Microscopy

The cells were fixed with 1% formaldehyde and 0.2% glutaraldehyde in PBS (50 mM K-phosphate, 0.9% NaCl, pH 6.9) for 1 h on ice. After several washing steps in PBS, cells were embedded following the progressive lowering of temperature (PLT) method (17). Cells were dehydrated with 10%, then 30% ethanol for 30 min on ice, then with 50% ethanol for 30 min at −20° C., and 70%, 90%, 100% ethanol for 30 min each at −35° C., and with 100% ethanol for 1 h at −35° C. Infiltration with the Lowicryl resin K4M was done as follows: 1 part ethanol/1 part K4M resin for overnight at −35° C., 1 part ethanol/2 parts K4M resin for 12 h and pure K4M resin for 2 days at −35° C. with several changes of the resin mixture. Polymerisation of the resin was achieved with UV-light (366 nm) for 1 day at −35° C., and at room temperature for another 2 days. Ultrathin sections were poststained with uranyl acetate and lead citrate before they were examined with a Zeiss EM 10B transmission electron microscope at an acceleration voltage of 80 kV.

RESULTS

Figure 2:
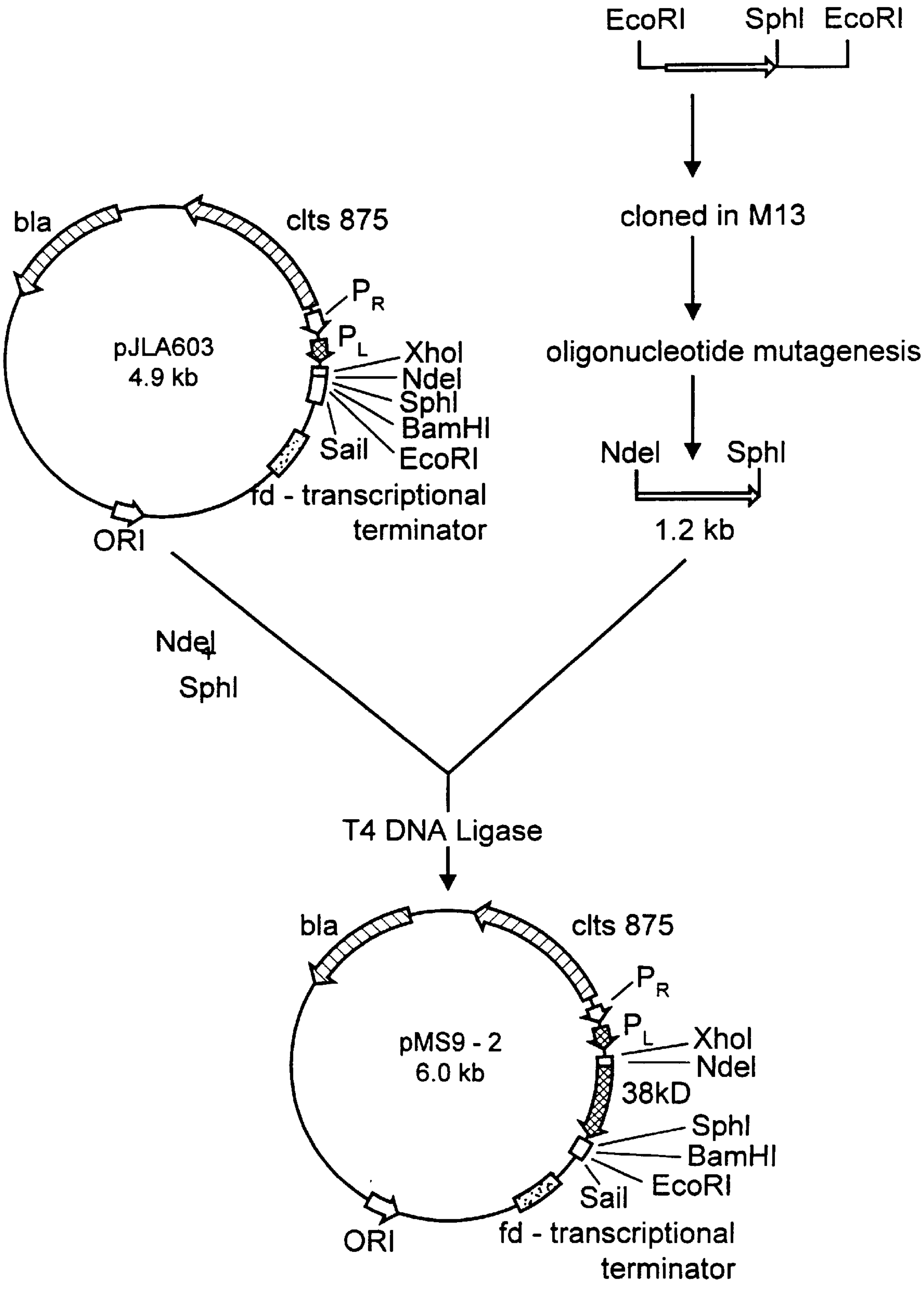
FIG. 2. Construction of expression plasmids. A 2.0 kb EcoRI fragment containing the gene for the 38 kDa protein was cloned from lambda AA59 (3) into M13mp19 and mutagenized to create a NdeI (CATATG) in such a way that it included the initiation codon of the gene. A 1.2 kb NdeI-SphI fragment was then subcloned into the NdeI-SphI site of the expression vector, pJLA603, which contains the bacteriophage lambda $P_R$ and $P_L$ promoters in tandem, the atpE translation initiation region (white box), the fd transcriptional terminator and translational stop codons in all the three reading frames (Schauder, B., H. Blöcker, R. Frank, and J. E. G. McCarthy. 1987. Inducible expression vectors incorporating the *Escherichia coli* atpE translational initiation region. Gene. 52: 279–283). Plasmids are not drawn to scale.

Construction of expression plasmids. The DNA sequence of the 38 kDa gene revealed an open reading frame encoding a polypeptide of 374 amino acids and containing GTG as the initiation codon (Andersen, A. B., and E. B. Hansen. 1989. Structure and mapping of antigenic domains of protein antigen b, a 38,000-molecular-weight protein of *Mycobacterium tuberculosis*. Infect. Immun. 57: 2481–2488). There is also a 24 amino acid long signal sequence (FIG. 1A) showing similarity to those of bacterial lipoproteins. In the present study, the gene was manipulated so that high level expression of the unfused 38 kDa antigen could be achieved in the pJLA603 expression vector (8; FIG. 2). For cloning and expression in these vectors, it is required that the foreign gene contains a restriction site, e.g., NcoI, NdeI, SphI, which includes an in-frame ATG within its recognition sequence. Since there is no such site around the initiation codon of the 38 kDa gene, oligonucleotide mutagenesis in M13mp19 was carried out to create an NdeI site at the N-terminus and to change the initiation codon from GTG to ATG (FIG. 1 and 2). The 1.2 kb NdeI-SphI fragment that could be excised from the M13 derivative after mutagenesis was then cloned between the NdeI-SphI sites of pJLA603. The recombinant plasmid, which was designed to express the 38 kDa protein with its original signal peptide intact, was designated pMS9-2. In the same way, another recombinant plasmid pMS10-4 containing a deletion of the first 6 amino acids in the signal sequence was constructed (FIG. 1C). Computer analysis of the translation initiation region of pMS9-2-specified mRNA predicted a loose secondary structure (FIG. 1B) which should be highly suitable for high level expression in *E. coli* (McCarthy, J. E. G., and C. Bokelmann. 1988. Determinants of translational initiation efficiency in the atp operon of *Escherichia coli*. Molec. Microbiol. 2: 455–465). On the other hand pMS10-4 showed a more stable secondary structure (FIG. 1D) indicating that the expression from this plasmid might not be as good as from pMS9-2. Both recombinant plasmids were used for expression studies.

Expression of the Recombinant Antigen in Small-Scale Culture

Figure 3:
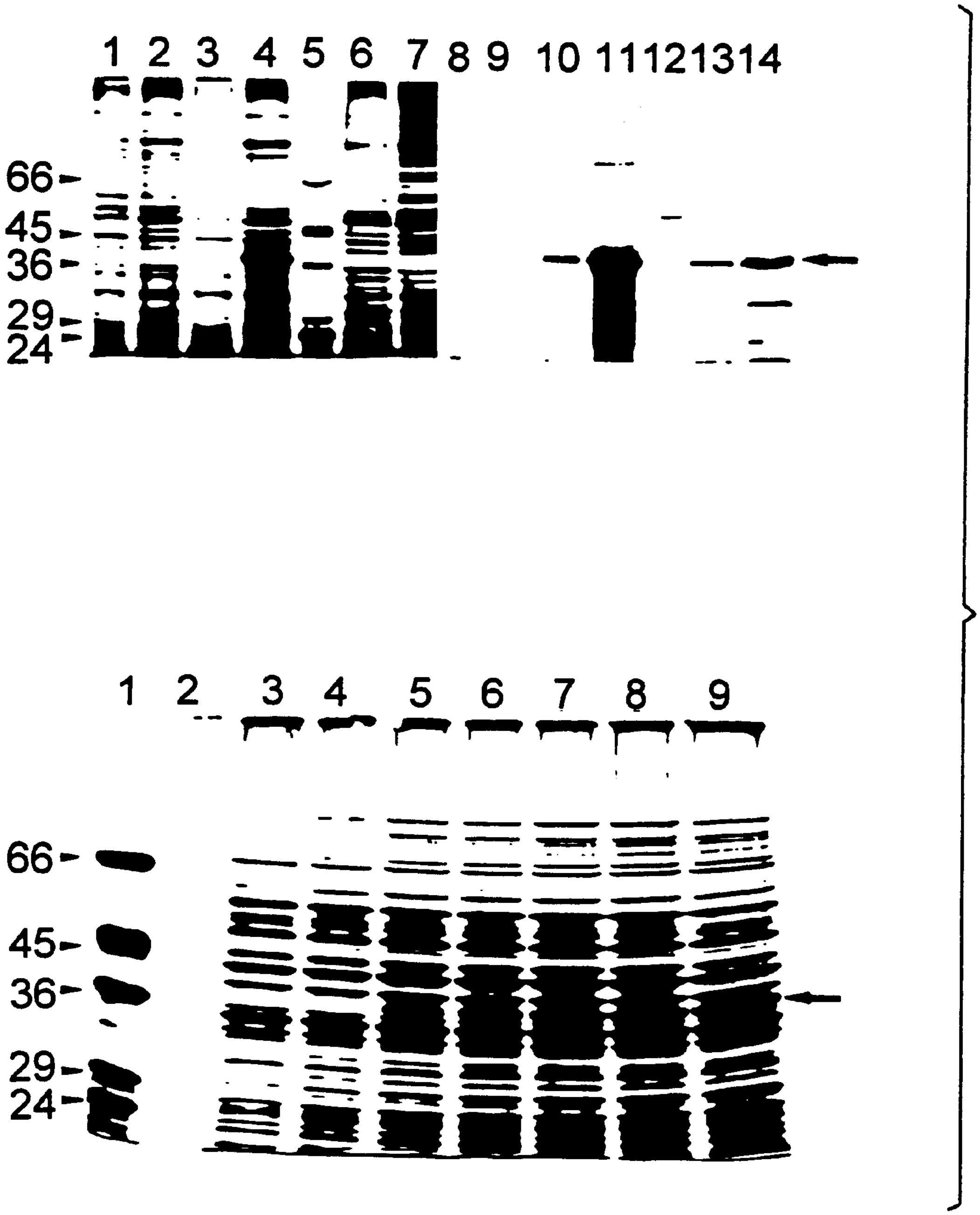
FIG. 3. Expression of the recombinant 38 kDa protein in *E. coli* CAG629 in batch cultures (A) and in a bioreactor (B). A, silver stained gels (lanes 1–7) and the corresponding immunoblots with MAb HBT12 (lanes 8–14) showing the proteins produced by CAG629 (pMS9-2) after growth at 30° C. (lanes 1/8 and 2/9), at 42° C. (lanes 3/10 and 4/11). The protein patterns of CAG629 (pMS10-4) after induction at 42° C. are shown in lanes 6/13 and 7/14. Lanes 1, 3, and 6 represent the soluble fractions and lanes 2, 4, and 7 the inclusion bodies. Lanes 5, molecular weight markers (values given on the left are in kilodaltons), 12 (prestained standard). B, accumulation of the recombinant 38 kDa protein in the bioreactor at 30° C. (lane 3) and after induction at 42° C. (lanes 4–9). Samples were withdrawn every 30 min after induction. Lanes 1 shows the molecular weight marker and lane 2 small amount of 38 kDa protein purified from inclusion bodies of a batch culture of CAG629(pMS9-2). The arrow marks the double band corresponding to the recombinant product.

Several *E. coli* strains (DH5ζ; EC538 and CAG629) were tested for expression of the 38 kDa recombinant antigen encoded by pMS9-2 and pMS10-4. The lon, htpR strain CAG629 showed the strongest expression. Extracts of CAG629(pMS9-2) cells induced at 42° C. contained substantial amounts of the recombinant protein (FIG. 3, lane 3, and 4) whereas it was absent in extracts from uninduced cells (FIG. 3, lane 1). The recombinant strain exhibited no obvious perturbations after induction and continued to grow exponentially (data not shown). Immunoblotting with MAbs HBT12 (FIG. 3A, lanes 10, and 11), HAT2 and HYT28 (data not shown) yielded positive reactions with the recombinant 38 kDa protein. Most of the recombinant protein was present in the cell pellet fraction of disrupted cells and only a small fraction was detected in the supernatant fluid (FIG. 3A, lanes 10, 11). The recombinant clone CAG629(pMS10-4), as expected from the secondary structure prediction, produced considerably less protein than pMS9-2 (FIG. 3A, lanes 13, 14). The faint bands seen on the immunoblots which run slower than the 38 kDa protein correspond to SDS-insoluble, aggregated forms of the recombinant protein.

Figure 4:
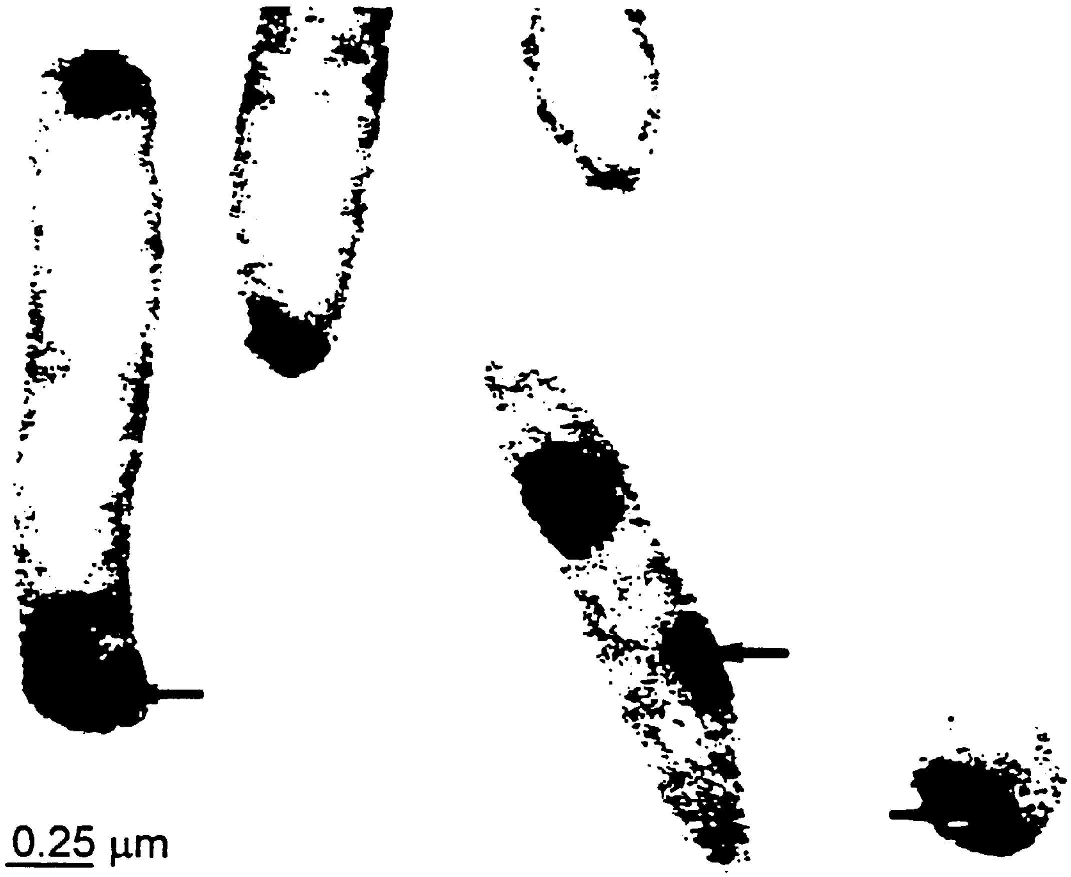
FIG. 4. Electron micrograph of sections of CAG629 (pMS9-2) showing inclusion bodies (arrows).

The recombinant 38 kDa protein was produced at high levels (about 10% of the total cellular protein) as measured by laser densitometry of the silver stained SDS-PAGE gels. As is often the case with recombinant proteins produced at high levels in *E. coli* (Halenbeck, R., E. Kawasaki, J. Wrin, and K. Koths. 1989. Renaturation and purification of biologically active recombinant human macrophage colony-stimulating factor expressed in *Escherichia coli*. Biotechnology 7: 710–715; Sarmientos, P., M. Duchesne, P. Denefle, J. Boiziau, N. Fromage, N. Delaporte, F. Parker, Y. Lelievre, J-F. Mayaux, and T. Cartwright. 1989. Synthesis and purification of active human tissue plasminogen activator from *Escherichia coli*. Biotechnology 7: 495–501), the 38 kDa antigen was mostly contained in cytoplasmic aggregates or inclusion bodies (FIG. 4).

Fermentation of Recombinant *E. coli* and Purification of the Recombinant Antigen Recombinant clone CAG629(pMS9-2) was chosen for a 30 L fermentation because it produced and tolerated the antigen at high levels in batch cultures, and coded for the 38 kDa protein with an intact signal sequence. The time course of production of the recombinant antigen in the bioreactor was monitored (FIG. 3B). SDS-PAGE of the whole cell extracts showed that within 30 min after increasing the temperature from 30° C. to 42° C., a double band of 38 kDa size was clearly visible on silver stained gels.

Figure 5:
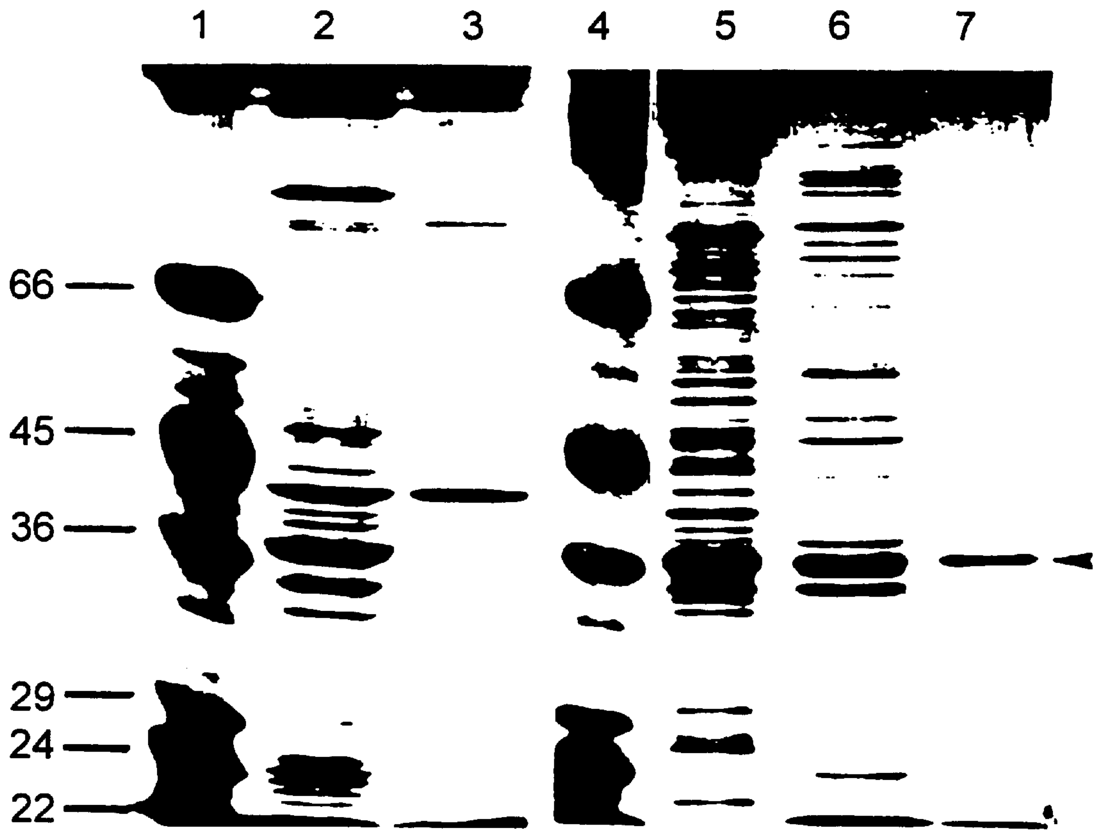
FIG. 5. SDS-12.5% PAGE (silver stain) analysis of different purification steps. Lanes 1 and 4 show the molecular weight standards. Lane 2, solubilized inclusion bodies; lane 3, proteins released during washing of inclusion bodies before solubilization; lane 5, proteins renatured on a cross-linked dextran; SEPHADEX G-25; lane 6+7, QAE-polysaccharide; SEPHAROSE, Pharmacia Fine Chemicals AB, Uppsala, Sweden, eluates;. The arrow indicates the 38 kDa recombinant protein.
Figure 6:
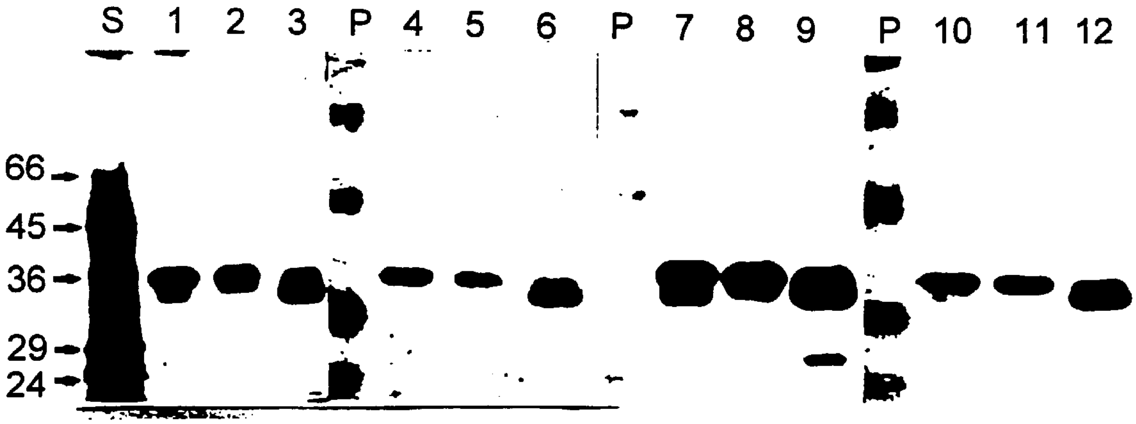
FIG. 6. SDS-PAGE and immunoblot analyses of the FPLC-purified 38 kDa protein preparations. Samples containing about 1 μg protein were separated by SDS-12.5% PAGE and either silver stained (lanes 1–3), or immunoblotted using anti-38 kDa MAbs: HAT2 (lanes 4–6), HBT12 (lanes 7–9), and HYT28 (lanes 10–12). The recombinant protein that reacted with the three MAbs was found in two main peaks: one at 100 mM NaCl (lanes 1, 4, 7, and 10), and the other at 130–200 mM NaCl (lanes 3, 6, 9, and 12). Lanes 2, 5, 8, and 11 show the protein purified in presence of octylphenoxy polyoxyethanol; TRITON X-100 (eluting at 170 mM NaCl). The molecular weight standard is in lane S (in kilodaltons as shown on the left), and the lane P represents the pre-stained marker used during immunoblotting.

Washing of the inclusion bodies obtained from the fermentor culture with buffer containing TRITON X-100 resulted in the removal of some of the contaminating proteins (FIG. 5, lane 3) without any apparent loss of the recombinant antigen (FIG. 5, lane 2). Using a SEPHADEX G-25, supra column the antigen was desalted and renatured (FIG. 5, lanes 6); we did not observe any reaggregation of the antigen at this stage. Further purification of the antigen was obtained by multiple rounds of FPLC-anion-exchange chromatograpy (FIG. 6) where the antigen was found to elute at 100 mM NaCl (Preparation I) and between 130–200 mM NaCl (Preparation III). Preparation II shown in FIG. 6 represents the antigen purified on FPLC-anion-exchange column in presence of TRITON X-100 from the aggregated and contaminated fractions obtained from earlier anion-exchange chromatographic steps.

Structure, immunological reaction and immunogenicity of purified recombinant protein. The immunological reactions of the purified antigen preparations were tested with monoclonal antibodies HAT2, HBT12 and HYT28. All the three antibodies reacted with recombinant antigen preparations (FIG. 6). When the affinity purified native antigen was compared with the recombinant antigen (Preparation I) by SDS-PAGE and immunoblotting, no difference was observed (FIG. 7A). The silver stained gel and the immunoblot shown in FIG. 7A were also traced with a laser densitometer and, after normalizing for differences in the amounts of protein present, the native and the recombinant antigen were seen to have given identical reactions with the monoclonal antibodies HBT12 (FIG. 7B), HAT2 and HYT28 (data not shown).

Figure 8A:
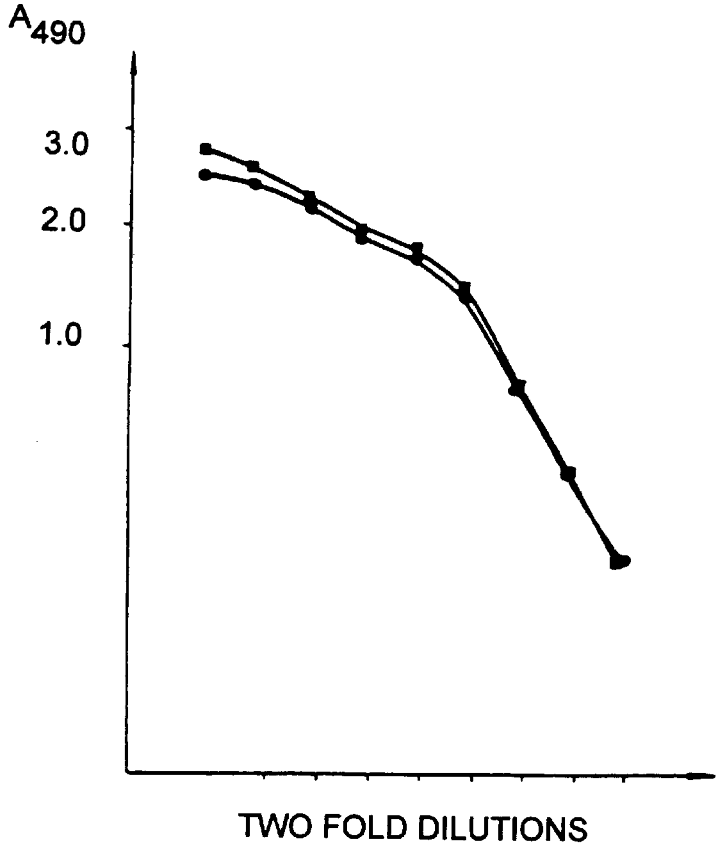
FIG. 8. Titration curves (A) of polyclonal sera with 38 kDa antigen. Sera from rabbits immunized with native 38 kDa protein (●) or recombinant 38 kDa protein (■). Serial two-fold dilutions starting with a 1:100 dilution were titrated in microtiter plates coated with the preparation I of recombinant 38 kDa protein (0.1 μg/well). Bound immunoglobulins were detected by horse radish peroxidase conjugated swine anti rabbit immunoglobulins diluted 1:1000 (P 217, Dakopatts, Glostrup, DK). B, as for A except that the microtiter plates were coated with the native 38 kDa antigen (0.1 μg/well).
Figure 8B:
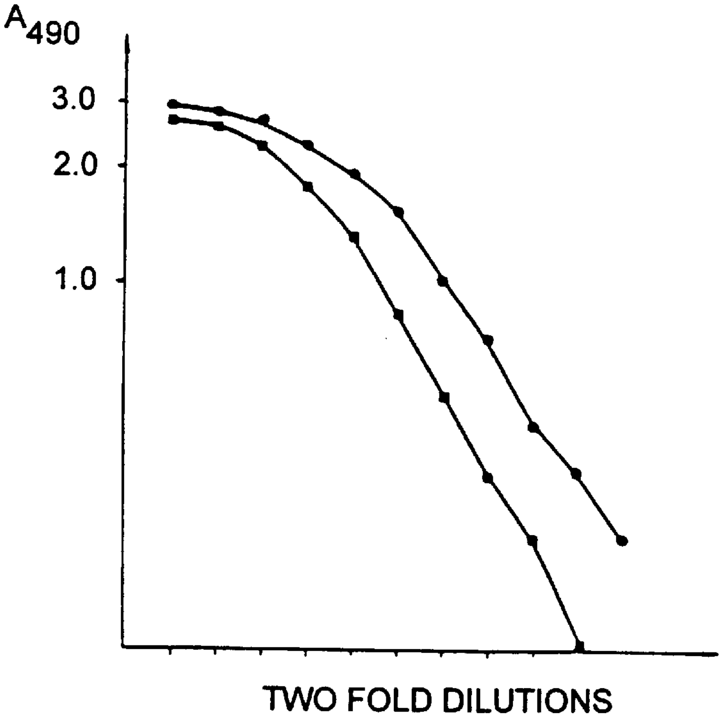

The immunogenicity of the recombinant antigen was also tested by raising polyclonal antisera in rabbits against the native and the recombinant antigen under similar conditions. The two sera were then assayed by enzyme linked immunosorbent assay (ELISA) against both recombinant (FIG. 8A) and native antigens (FIG. 8B). The slopes of the curves are identical showing that the two sera bind native and the recombinant 38 kDa protein equally well.

The amino acid composition of the 38 kDa recombinant protein closely resembles the amino acid composition derived from the nucleotide sequence (Table. 1)

About 33 kDa Protein

The deletion in comparison to the 38 kDa antigen has completely removed the signal sequence. Still, the truncated protein reacts strongly to the monoclonal antibodies HAT2, HBT12 and HYT28 showing that the three epitopes are intact. The truncated protein also shows strong reaction in ELISA and western blotting to sera from mice infected with *Mycobacterium tuberculosis*. We have found that about 85% of the sera from Tuberculosis patients reacted positively with the truncated protein and antigen, respectively, showing that the truncated antigen can be effectively used for the diagnosis.

DISCUSSION

A strategy was developed and implemented to clone a *Mycobacterium tuberculosis* DNA fragment in expression vector such that unfused 38 kDa protein would be produced at high levels. The vector contained the lambda $P_RP_L$ promoter and the efficient translation initiation region of the atpE gene which resulted in expression of the heterologous 38 kDa antigen gene in *E. coli* to a level representing 10% of the total cellular protein. About 15 mg recombinant protein/liter was produced under the conditions given. It should be emphasized, however, that the objective of the present work was to determine whether hyperproduced recombinant antigen could be recovered in an antigenic form immunologically indistinguishable from native antigen obtained from *Mycobacterium tuberculosis*, and not to optimize fermentation yields.

Most of the recombinant 38 kDa protein accumulated as inclusion bodies. 6M guanidine-HCl in the presence of a reducing agent (DTT) at high concentration was found to be suitable for the solubilization of the inclusion bodies. Renaturation of inclusion body proteins, specially hydrophobic, membrane proteins, is often difficult and needs careful optimization of experimental conditions. In our case, the usual procedure of dialysis or step-dialysis resulted in the precipitation of the recombinant 38 kDa protein even at very low protein concentrations (0.05 mg/ml). Renaturation of the recombinant protein on SEPHADEX G-25, supra proved on the other hand to be effective and no significant reaggregation of the protein was observed. Starting with inclusion bodies containing about 200 mg total protein, we were able to purify 19 mg of the 38 kDa antigen with more than 95% purity as judged by silver staining of SDS-polyacrylamide gels.

The 38 kDa antigen of *M. tuberculosis* is most probably a lipoprotein (D. B. Young and T. R. Garbe, Res. Microbiol. 142: -, 1991, in press). Lipoproteins show aberrant, diffuse bands on SDS-PAGE gels (Pugsley, A. P., C. Chapon, and M. Schwartz. 1986. Extracellular pullulanase of *Klebsiella pneumoniae* is a lipoprotein. J. Bacteriol. 166: 1083–1088; Schouls, L. M., R. Mount, J. Dekkert, and J. D. A. van Embden. 1989. Characterization of lipid-modified immunogenic proteins of *Treponema palidum* expressed in *Escherichia coli*. Microbial. Pathogen. 7: 175–188). As is true of other lipoproteins, we observed a strong tendency of the recombinant 38 kDa antigen to aggregate during anion-exchange chromatography and during concentration by ultrafiltration. Part of the antigen which aggregated during ultrafiltration could be recovered by solubilization in 2% TRITON X-100, supra followed by FPLC on MonoQ.

The native 38 kDa protein runs as a doublet on SDS-polyacrylamide gels. The reason for this is not known but it might be due to acylation and processing of the pre-protein. We did not remove the signal sequence before producing the antigen in large amounts because the presence of the lipoyl moities on the N-terminal cystein may play important role in the immunogenicity of protein antigens (Deres, K., H. Schild, K-H-Wiesmüller, G. Jung, and H-G. Ramensee. 1989. In vivo priming of virus-specific cytotoxic lymphocytes with synthetic lipopeptide vaccine. Nature. 342: 561–564). The recombinant protein purified in this study also showed the doublet characteristic. Preparation I contains mostly the upper band and only minor amounts of the lower band. Preparation II contains both the upper and the lower bands in almost equal amounts. Preparation III represents a proteolytically truncated derivative (34 kDa) of the 38 kDa antigen.

The native 38 kDa protein isolated from the culture supernatant of *M. tuberculosis* and the purified recombinant proteins present in preparations I and II are of the same size and show the doublet character on SDS-PAGE. Furthermore, the purified proteins and the native antigen showed identical reaction on immunoblots with monoclonal antibodies HAT2, HBT12, and HBT28. Polyclonal serum raised against the recombinant protein (Preparation I) recognized the native antigen and showed the same reaction in ELISA as the serum raised against the native antigen. Similar results were obtained when the two sera were tested against the recombinant antigen by ELISA demonstrating that the recombinant protein posseses similar epitopes and is as immunogenic as the native 38 kDa protein purified from *M. tuberculosis.*

In conclusion, we have developed an expression system and production and purification procedure for the 38 kDa protein of *M. tuberculosis* in *E. coli* that enable the ready isolation of significant quantities of the antigen. The recombinant antigen is immunologically indistinguishable from the native antigen. These results should significantly accelerate assessment of the utility of the antigen for diagnosis and vaccine development.

| Living Material | |
|---|---|
| Lambda-AA59: | genomic clone for 2.0 kb EcoRI fragment<br>Supply: Literature (3); DSM 6524 |
| M13mp19: | Phagen for transferring a 2.0 kb EcoRI fragment<br>Supply: Pharmacia |
| pJLA603: | Vector for inserting a NdeI-SphI fragment of M13mp19 after transferring the 2.0 kb EcoRI fragment and mutagenization<br>Supply: Literature (20); Medac (Hamburg) |

TABLE 1

Amino acid composition of purified 38kDa antigen

| Amino acid | no. of residues: Deduced from DNA sequence | no. of residues: Amino acid analysis |
|---|---|---|
| Ala | 55 | 56.8 |
| Arg | 5 | 6.9 |
| Asn | 18 | 39.3 |
| Asp | 16 | |
| Cys | 3 | ND[a] |
| Gln | 19 | 32.8 |
| Glu | 10 | |
| Gly | 43 | 41.2 |
| His | 7 | 7.6 |
| Ile | 19 | 17.8 |
| Leu | 36 | 32.4 |
| Lys | 12 | 12.5 |
| Met | 6 | 0.7 |
| Phe | 13 | 13.0 |
| Pro | 26 | 23.4 |
| Ser | 26 | 22.3 |
| Thr | 27 | 23.8 |
| Trp | 4 | ND |
| Tyr | 10 | 10.8 |
| Val | 19 | 19.0 |

[a]ND Not determined

We claim:

1. Isolated and purified 38 kDa antigen of wild type (pre-protein) *Mycobacterium tuberculosis* which is produced by *Escherichia coli* comprising a hybrid plasmid having a DNA coding 17, 18, 19, 20, 21 or 22 amino acids of the 38 kDa antigen (pre-protein) and having a restriction site within its recognition sequence comprising the base triplet ATG, wherein the 17, 18, 19, 20, 21 or 22 amino acids comprise contiguous 16, 17, 18, 19, 20 or 21 amino acids of the SEQ. ID NO. 1 and in addition said base triplet ATG starting from the N-Terminus of the produced protein.

2. Isolated and purified 38 kDa antigen (pre-protein) according to claim 1, wherein the DNA sequence coding the 38 kDa antigen (pre-protein) is inserted upstream in a NcoI-, NdeI- or SphI-restriction sequence of the starting vector of the expression plasmid.

3. Isolated and purified 38 kDa antigen (pre-protein) according to claim 1, wherein the DNA sequence coding the 38 kDa antigen (pre-protein) is in accordance with FIG. 1A or FIG. 1C of the accompanying drawings.

4. Isolated and purified 38 kDa antigen according to claim 1 and renatured as follows:

solubilization of the antigen obtained as inclusion body in guanidine-HCl; and subsequent renaturation by means of chromatography.

5. Isolated and purified 38 kDa antigen (pre-protein) according to claim 4, wherein the solubilization has been carried out with about 6 M guanidine-HCl in the presence of dithiothreitol.

6. Isolated and purified 38 kDa antigen (pre-protein) according to claim 1 which comprises 22 to 17 amino acids of the SEQ ID NO. 1.

7. Isolated and purified protein of about 33 KDa which is obtainable by means of *Escherichia coli* as host of pJLA 603 as expression plasmid, a DNA SEQ. ID NO. 1 coding the 38 kDa antigen of wild type *Mycobacterium tuberculosis* (pre-protein) being inserted into a NcoI-, NdeI- or SphI- restriction site of pJLA 603, the inserted DNA sequence comprising the whole signal sequence of the antigen and a recognition sequence within its restriction site comprising the base triplet ATG, coding M (+1 of pre-protein).

8. Isolated and purified protein of about 33 kDa according to claim 7, being deleted N-terminally by the signal sequence (1–23) and additional 24 amino acids (24–47) compared with the 38 kDa antigen (pre-protein) of wild type *Mycobacterium tuberculosis* such that the N-terminus is S (+48 pre-protein).

9. Isolated and purified protein of about 33 kDa produced simultaneously with 38 kDa antigen and being separated from 38 kDa antigen according to claim 1 and renatured as follows:

solubilization of the protein, obtained as inclusion body in guanidine-HCl; and subsequent renaturation by means of chromatography.

10. Isolated and purified protein of about 33 kDa according to claim 9, wherein the solubilization has been carried out 6 M guanidine-HCl in the presence of dithiothreitol.

11. Isolated and purified protein of about 33 kDa according to claim 9, separated from simultaneously expressed 38 kDa antigen.

12. The protein of claim 9 wherein solubilization is carried out in the presence of a reducing agent.

* * * * *